US00PP15059P3

(12) United States Plant Patent
Kordes

(10) Patent No.: US PP15,059 P2
(45) Date of Patent: Aug. 3, 2004

(54) MINIATURE ROSE PLANT NAMED 'KORLOBEA'

(50) Latin Name: *Rosa hybrida*
Varietal Denomination: KORlobea

(75) Inventor: Tim-Hermann Kordes, Offenseth-Sparrieshoop (DE)

(73) Assignee: W. Kordes Sohn Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 79 days.

(21) Appl. No.: 10/078,769

(22) Filed: Feb. 19, 2002

(65) Prior Publication Data

US 2003/0163858 P1 Aug. 28, 2003

(51) Int. Cl.[7] ..... A01H 5/00
(52) U.S. Cl. ..... Plt./121
(58) Field of Search ..... Plt./116, 121, 122

*Primary Examiner*—Howard J. Locker
(74) *Attorney, Agent, or Firm*—Webb Ziesenheim Logsdon Orkin & Hanson, P.A.

(57) ABSTRACT

A new miniature rose plant which has abundant, pink colored flowers and attractive foliage. The variety successfully propagates from softwood cuttings and is suitable for year round production in commercial glasshouses as a flowering pot plant.

2 Drawing Sheets

Varietal Denomination: 'KORlobea'

BACKGROUND OF THE NEW PLANT

The present invention constitutes a new and distinct variety of miniature rose plant which was developed by artificially pollinating an unnamed seedling (unpatented) with an unnamed seedling (unpatented).

The objective of the hybridization of this rose variety for commercial greenhouse culture was to create a new and distinct variety with:

1. Uniform and abundant flowers with good keepability;
2. Attractive long lasting foliage and compact growth;
3. Year round flowering under glasshouse conditions;
4. Suitability for production from softwood cuttings in pots; and
5. Durable flowers and foliage which make the variety suitable for distribution in the floral industry.

This combination of qualities was not present in previously available commercial cultivars of this type and distinguish 'KORlobea' from other varieties.

The two parents were crossed in the summer of 2000 and the resulting seed was sown in December 2000 in a controlled glasshouse environment. The seeds from the hybridization were planted in a controlled environment in Klein Offenseth, Sparrieshoop, Germany and evaluations were conducted on the resulting plants. The instant cultivar originated as a single plant from the stated cross.

Asexual reproduction of 'KORlobea' by cuttings was first done in Denmark and later in California in controlled greenhouse environments. The characteristics of the new variety remain true to type through successive propagations.

The new rose variety may be distinguished from its seed parent, an unnamed breeding seedling, by the following combination of characteristics:

1. 'KORlobea' has big double flowers, while the seed parent has medium sized single flowers.
2. 'KORlobea' has pink colored petals, while the seed parent has light orange-red colored petals.

The new variety may be distinguished from its pollen parent, an unnamed breeding seedling, by the following combination of characteristics:

1. 'KORlobea' has bigger flowers and foliage as compared to the pollen parent.
2. 'KORlobea' has light pink colored petals, while the pollen parent has dark pink colored petals.

The new variety differs from 'KORfrauma', U.S. Plant Pat. No. 11,363, as set forth in Table 1:

TABLE 1

| | KORlobea | KORfrauma |
|---|---|---|
| Petal color, upper surface | 48D | 43A |
| Petal color, reverse surface | 48D | 53B |
| Petal count | 40 petals | 30–35 petals |

DESCRIPTION OF THE DRAWINGS

The accompanying color illustrations show as true as is reasonably to obtain in color photographs of this type, the typical characteristics of the buds, flowers, leaves, stems of 'KORlobea'.

In photo sheet #1.

Figures 1, 2, 3, 4, 5, 6, 7, 8, 9:
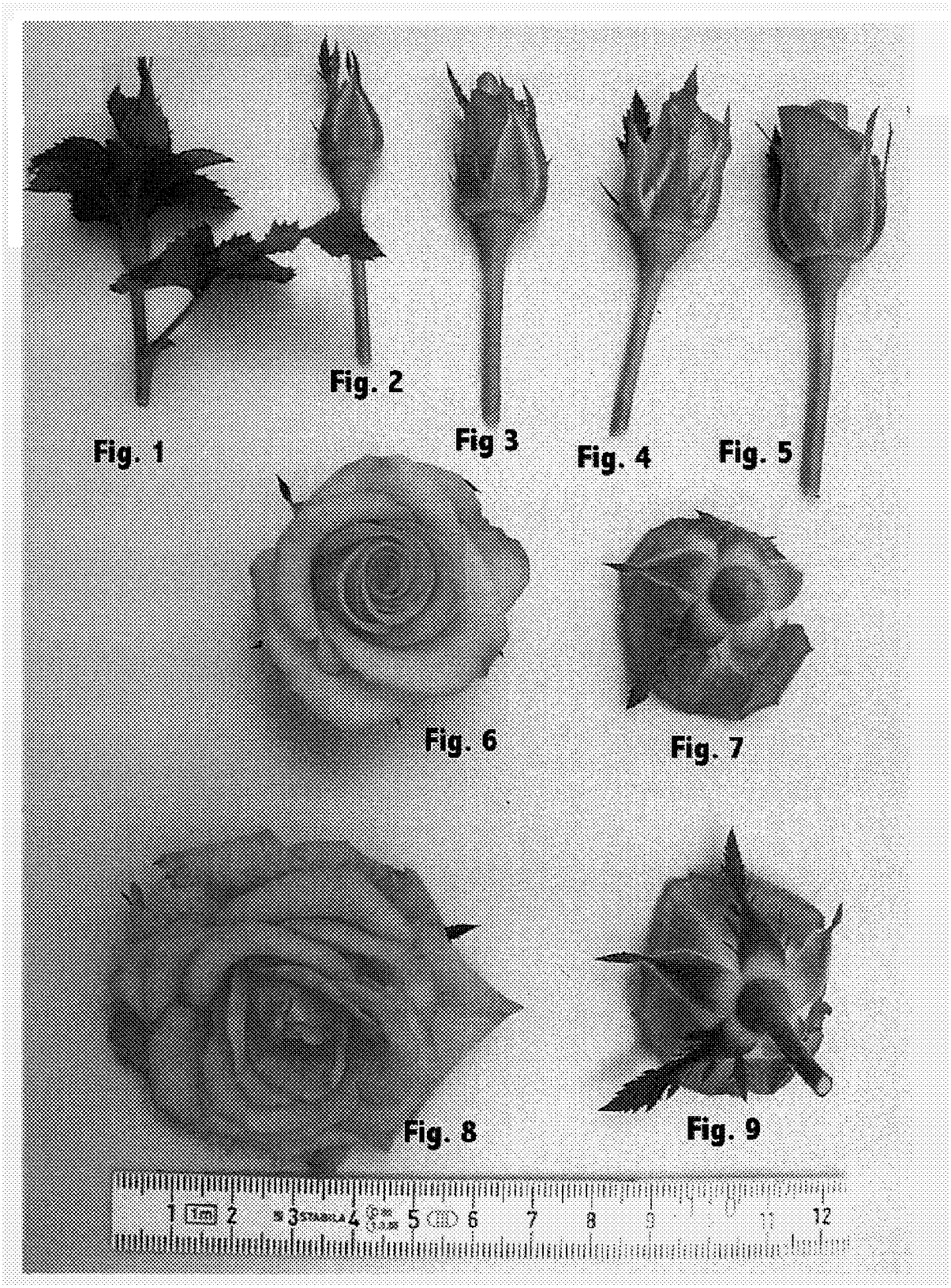
FIG. 1 shows a young shoot.
FIG. 2 shows a bud before opening of the sepals.
FIG. 3 shows a bud at the opening of the sepals.
FIG. 4 shows a bud at the opening of the petals.
FIG. 5 shows a flower during course of opening.
FIG. 6 shows an open flower, obverse plan view.
FIG. 7 shows an open flower, reverse plan view.
FIG. 8 shows a fully open flower, obverse plan view.
FIG. 9 shows a fully open flower, reverse plan view.
Figures 10, 11, 12, 13, 14, 15, 16, 17, 18:
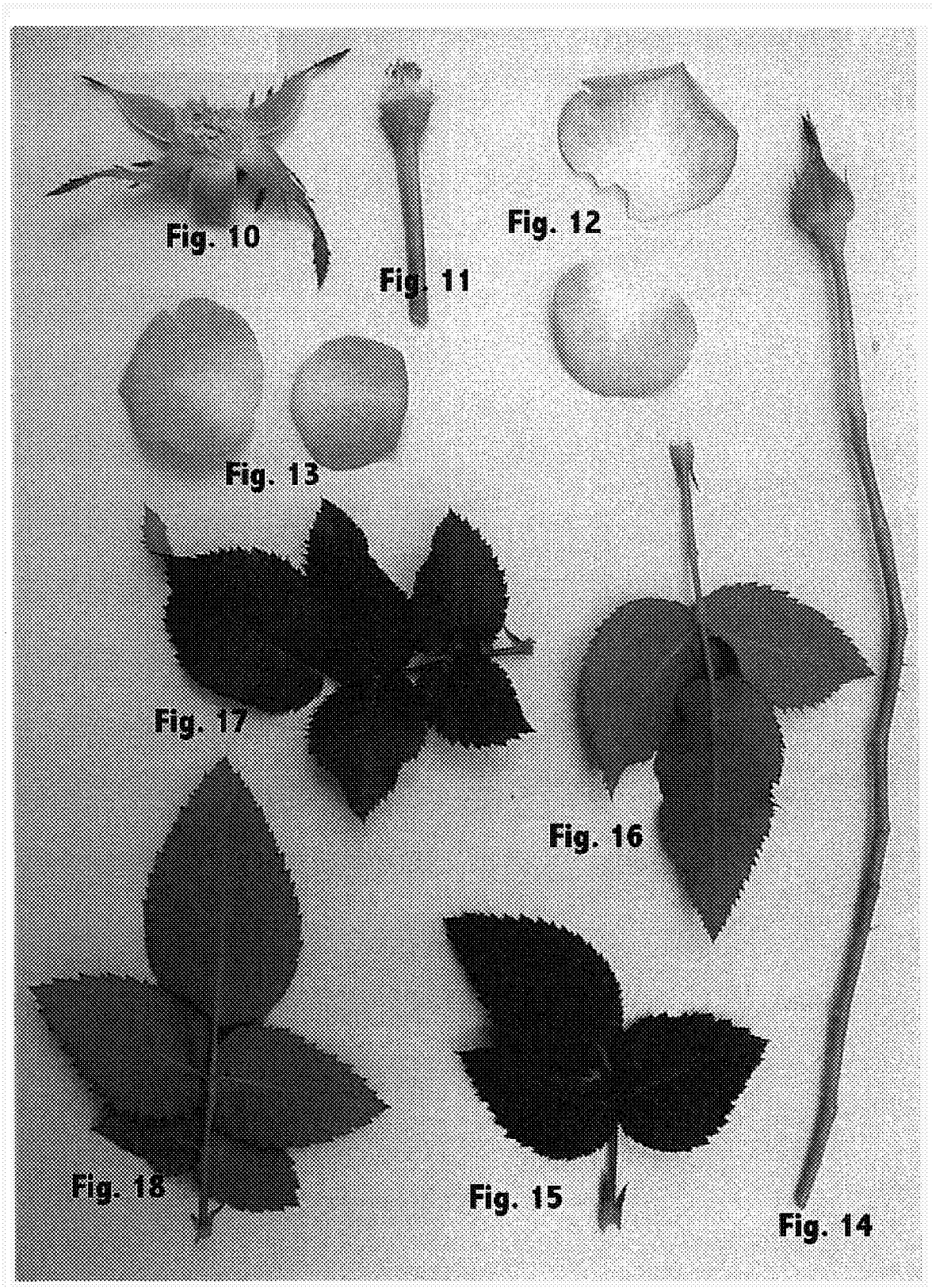

In photo sheet #2:

FIG. 10 shows a receptacle with stamens and pistils.
FIG. 11 shows a receptacle with pistils (stamens removed).
FIG. 12 shows detached flower petals, outer surface.
FIG. 13 shows detached flower petals, inner surface.

FIG. 14 shows a bare stem exhibiting thorns and flower attachment.

FIG. 15 shows three leaflets, upper side.

FIG. 16 shows three leaflets, under side.

FIG. 17 shows five leaflets, upper side.

FIG. 18 shows five leaflets, under side.

DESCRIPTION OF THE NEW PLANT

The following is a detailed description of 'KORlobea', as observed in its growth in greenhouses in Fraugde, Denmark and greenhouses in Santa Barbara, Calif. both at 20–25° C. Descriptions were made from plants 11 to 13 weeks old after propagation in a pot treated with growth regulators normally used in the greenhouse production process. The growth regulator Paclobutrazol was applied at 15–30 ppm weekly beginning at a plant age of 8 weeks. The peduncle length mentioned may actually be shorter and the foliage color several shades darker than on untreated specimens. Color references are made using The Royal Horticultural Society (London, England) Colour Chart, 1995, except where common terms of color are used.

THE PLANT

Classification:
- *Botanical.*—*Rosa hybrida.*
- *Commercial.*—Miniature rose.

Plant growth: Moderately vigorous. Grows compact upright to bushy. When grown as 10 cm pot plant, the average height of the plant is 18–20 cm, and average width is 20 cm. When grown as a 15 cm pot plant, the average height of the plant is 22–27 cm, and average width is 30 cm. Production time is generally 11–13 weeks depending on average temperature, light level, and cultural practices.

Stem:
- *Color.*—Young wood: 146C, with intonations of 178B. Older wood: 146B.
- *Thorns.*—Average number on main stems: 10. Average number on flowering stems: 10. Size: 3–4 mm. Color: 31C. Shape: Triangular and elongated.
- *Surface.*—Young wood: Smooth. Older wood: Smooth.
- *Stem diameter.*—3–4 mm.
- *Stem length.*—15 cm in a 10 cm pot; 20 cm in a 15 cm pot.
- *Internode length.*—15–20 mm.
- *Number of internodes.*—7–9.

FOLIAGE

Arrangement: Alternate, compound with 3–7 leaflets per leaf, generally symmetrical, abundant, and flat in aspect. Stipules at petiole base.

Quantity of leaves: 7–9 per lateral branch.

Leaf size for an average leaf having 5 leaflets:
- *Length.*—90–95 mm.
- *Width.*—70–75 mm.

Petioles:
- *Color.*—146C, with intonations of 183B.
- *Margin.*—Entire.
- *Length.*—11.5 cm.
- *Diameter.*—1–2 mm.

Stipules:
- *Size.*—5–6 mm.
- *Surface.*—Smooth.
- *Color.*—146C with stipitate glands.
- *Margin.*—Entire.

Rachis:
- *Color.*—146C, with intonations of 183B.
- *Margin.*—Margins with stipitate glands of 183B.
- *Length.*—15–20 mm.

Leaflets:
- *Margin.*—Double-serrated.
- *Shape.*—Ovate with acute apex and obtuse base.
- *Texture.*—Smooth.
- *Appearance.*—Dull.
- *Size.*—Length: 20–50 mm. Width: 15–30 mm.
- *Color.*—Young foliage. Upper surface: 137A. Lower surface: 197A, with intonations of 59B. Mature foliage: Upper surface: 133A. Lower surface: 198A.

INFLORESCENCE

Blooming habit: Recurrent.

Number of flowers: Generally 1 bud per flowering stem.

Peduncle:
- *Color.*—144A, with intonations of 59B.
- *Texture.*—Smooth and pubescent with few prickles.
- *Length.*—30–35 mm.
- *Form.*—Upright.

Receptacle:
- *Surface.*—Smooth, glabrous.
- *Shape.*—Funnel-shaped.
- *Size.*—Height: 5–6 mm. Width: 5–7 mm.
- *Color.*—143C.

Sepals:
- *Quantity.*—5.
- *Shape.*—Narrowly ovate with acute tip.
- *Texture.*—Leathery.
- *Margin.*—Foliaceous appendages on three of the five sepals.
- *Appearance.*—Dull.
- *Color.*—Upper surface: 146C. Reverse surface: 147B.

Buds:
- *Size upon opening.*—Height: 20–25 mm. Width: 15–20 mm.
- *Shape.*—Cupped; between urceolate and ovate.
- *Color.*—43B at one-fourth open.

Flower:
- *Duration.*—As a pot plant, flowers last 12–18 days.
- *Fragrance.*—None.
- *Size.*—45–50 mm in diameter.
- *Form* (*shape of flower when viewed from the side*).—Upon opening: Cupped. Open flower: Cupped.
- *Color.*—Petals, upon opening: Upper surface: 52C, with intonations of 47B. Reverse surface: 52C, with intonations of 47B. Petals, after opening: Upper surface: 48D, with intonations of 50A at edge. Reverse surface: 48C, with intonations of 50A.
- *Basal petal spots.*—Size: 4–5 mm. Color: 10D.
- *General tonality of open flower.*—43C on third day; 48D, with intonations of 50B afterwards.

Petals:
- *Petal reflex.*—Outermost petals reflex backwards at opening. When fully open, all petals reflex backwards.
- *Texture.*—Smooth.
- *Petal edges.*—Entire.
- *Petal count.*—Approximately 40 per flower.
- *Petal size.*—Length: 25 mm. Width: 40 mm.
- *Shape.*—Outer petals: Round. Inner petals: Ovate.
- *Petaloids.*—Generally none.

Reproductive organs:
- *Stamens.*—Number: Approximately 75–80 per flower. Pollen: Color: 15A. Abundance: Average amount.

Anthers: Size: 1–2 mm. Color: 59A. Shape: Oblong. Filaments: Size: 3–4 mm. Color: 12B.

*Pistils.*—Number: Approximately 30–35 per flower. Stigmas: Location: Superior in location to anthers. Color: 12B. Styles: Color: 57B. Length: 2–3 mm.

GROWTH

Vegetation: Dense.

Blooming: Abundant.

Aptitude to bear fruit: Poor.

Resistance to diseases: Above average resistance to mildew and Botrytis under normal growing conditions in Fraugde, Denmark and Santa Barbara, Calif.

Hips/seeds: Unknown, the plant has never been grown to the stage of seed development due to the fact that the variety is developed for use as a flowering potted plant only.

Winter hardiness and drought/heat tolerance: This variety is a potted flowering plant developed for indoor use only through one flowering period only and, due to lack of hardiness, it is not suitable to be used under outdoor conditions.

I claim:

1. A new and distinct variety of rose plant substantially as shown and described.

* * * * *